(12) United States Patent
Gedig et al.

(10) Patent No.: US 8,012,587 B2
(45) Date of Patent: Sep. 6, 2011

(54) COATING FOR VARIOUS TYPES OF SUBSTRATE AND METHOD FOR THE PRODUCTION THEREOF

(75) Inventors: Erk Gedig, Münster (DE); Lutz Haalck, Münster (DE)

(73) Assignee: Institut fur Chemo-und Biosensorik Munster E.V., Munster (DE)

( * ) Notice: Subject to any disclaimer, the term of this patent is extended or adjusted under 35 U.S.C. 154(b) by 0 days.

(21) Appl. No.: 10/333,737

(22) PCT Filed: Jul. 27, 2001

(86) PCT No.: PCT/EP01/08701
§ 371 (c)(1),
(2), (4) Date: Jul. 15, 2003

(87) PCT Pub. No.: WO02/10759
PCT Pub. Date: Feb. 7, 2002

(65) Prior Publication Data
US 2005/0042455 A1 Feb. 24, 2005

(30) Foreign Application Priority Data
Jul. 28, 2000 (DE) .............................. 100 36 907 U

(51) Int. Cl.
*B32B 27/08* (2006.01)
*B32B 31/00* (2006.01)
(52) U.S. Cl. .................. 428/411.1; 428/474.4
(58) Field of Classification Search ............... 428/474.4, 428/411.1
See application file for complete search history.

(56) References Cited

U.S. PATENT DOCUMENTS
2002/0128234 A1* 9/2002 Hubbell et al. ............... 514/100
* cited by examiner

*Primary Examiner* — Thao T. Tran
(74) *Attorney, Agent, or Firm* — Bacon & Thomas, PLLC

(57) ABSTRACT

The invention refers to coatings on different substrates, whereby a hydrophilic polymer layer is bound by means of a polymer adhesion promoter layer to a substrate. A method for the production of these layer systems is disclosed as well. The layers according to the invention can be used as immobilization matrix and for the suppression of non-specific protein adsorption in biosensors, MALDI targets and other bioanalytical devices. Furthermore they can be used for the biocompatibilization of implants and for the coating of contact lenses. Optical elements, which are provided with such coatings, do not fog up any more. Beyond that the layers are dirt-deflecting and/or self-cleaning.

20 Claims, 15 Drawing Sheets

—————— Uncoated Gold Surface

- - - - - - Carboxymethyldextran 20 kDa,   Brush Conformation

1: PBS buffer, pH 7.4
2: 1 mg BSA / ml PBS buffer
3: PBS buffer, pH 7.4
4: Fetal calf serum, undiluted
5: PBS buffer, pH 7.4

– – – – Carboxymethyldextran MW 500 kDa
············ Carboxymethyldextran MW 20 kDa
———— Carboxymethylxylitol (planar)

1: 10 mM Sodium Acetate Buffer pH 5.0

2: 50 µg BSA/ml 10 mM Sodium Acetate Buffer pH 5.0

3: 10 mM Sodium Acetate Buffer pH 5.0

4: 2M NaCl, 10 mM NaOH

5: Sodium Acetate Buffer pH 5.0

COATING FOR VARIOUS TYPES OF SUBSTRATE AND METHOD FOR THE PRODUCTION THEREOF

FIELD OF THE INVENTION

The submitted invention concerns polymer coatings for different substrate surfaces, in order to increase their bioinert character. Such substrate coatings are frequently used for devices, which are in contact with biological media, e.g. bioanalytic devices or implants. Surfaces are hereby preferred that are bioinert as far as possible, i.e. with low interactions.

BACKGROUND OF THE INVENTION

State of the art substrate coatings used are usually hydrophilic polymers, some members of this group being polyethers, e.g. polyethyleneglycol; polysaccharides, such as hepaiin or dextran; polyalcohols, e.g. polyvinyl alcohol; or also polyamides, as for example polyacrylamide.

Thin hydrogel layers from carboxylated polysaccharides have proofed themselves for biosensory pur U.S. Pat. No. 5,436,161), since these do not only shield the sensor surface against nonspecific interactions, but also make it possible through the carboxyl functionalities to efficiently immobilize different biomolecules.

SUMMARY OF THE INVENTION

The method used for the binding of the polymers to the substrate usually depends on the used substrate material.

A reactive silane is usually first bound to glass or other oxidic surfaces (silanisation), to which a hydrophilic polymer is then coupled in a second step. The production of high-quality silane layers however makes the employment of organic solvents necessary and is relatively labor-consuming.

Noble metals can be functionalized through a monolayer of bisfunctional long-chain alkylmercaptans. Thin polysaccharide layers are then bound covalently to the activated functional groups, which are carboxymethylated later for the introduction of coupling capable functionalities. Punctual inhomogeneities, the so called pinhole defects, arise, since the self-organizing monolayer follows the nano-roughness of the metal surface. Further, the density of the carboxyl functions introduced later cannot be adjusted or only be adjusted with difficulty.

Plastic substrates can be unselectively functionalized through the employment of oxidizing agents, plasma or ionizing radiation. Further, polyamines were adsorbed in thin layer, to which then polyethylenglycol (PEG) could be bound covalently (Bergstrom et al. (1992) *J. Biomed. Mat. Res.*, 26, 779-790).

A disadvantage of this method however is the fact that only the terminal functional group of the PEG chain is available for the subsequent covalent immobilization of ligands.

The immobilization density of polyethylenglycol also is not particularly high due to the same reason.

A substrate-independent possibility for surface derivatization consists in the plasma deposition of thin polymer films of suitable functionality on the substrate with subsequent covalent bonding of the desired hydrophilic polymer through oxirane groups (WO 94/06485). This method requires a relatively complex apparative set-up and in addition frequently only results in small densities of reactive groups. Further the thickness of the deposited polymer layers is hard to control.

A similar approach is described in U.S. Pat. No. 5,080,924. Here it also comes to a very low immobilization density of the hydrophilic polymer on the underlying adhesion promotor layer. The reason for this is the low concentration of the polysaccharide, which leads to the fact that the polymer chains align themselves parallel to the substrate surface, thus yielding only a small layer thickness.

Further, multi-layered self-organized polyelectrolyte-layers which are applied on a substrate in alternating fashion are described for example in DE 40 26 978 A1. The polymer chains are present here in train configuration (parallel to the surface) and/or train loop configuration (partly flat on the surface, partly loop-like oriented), respectively. These techniques of alternating polyelectrolyte-adsorption as well as their variants only lead to a small layer thickness growth per step (few nm). The arrangement of the polymer chains parallel to the surface leads to two-dimensional structures with small immobilization capacity. Beyond that, biomolecules, which are larger than few kDa, cannot, or only with difficulties, diffuse through these layers (filter effect).

The aim of the invention is to make available a coating for different substrates with which nonspecific adsorptions can be avoided, obtaining at the same time an adjustable immobilization capacity.

The coating according to invention with the described characteristics can be produced by first covering the cleaned substrate with a thin polymeric adhesion mediator layer, to which a further hydrophilic polymer layer from at least one polymer is coupled, their polymer chains aligned at least partly vertical to the substrate surface, thus, brush-like. The imnobilization capacity of this layer towards e.g. biomolecules can be adjusted on the basis of the portion of the brush-like aligned polymer chains.

The hydrophilic polymer layer can consist of different polymers. This has the advantage that the perrneability of the hydrophilic polymer layer can be adjusted for biomolecules with different molecular weights. This is done by adjusting the concentration ratio between low- and high-molecular polymers, which build up the hydrophilic polymer layer, according to the molecules to be analyzed.

It is further possible to manufacture mixed hydrogel layers by mixing several different hydrophilic polymers. The polymers can differ both in chemical composition, the charge or molecular weight. In this way layers with differently charged microscopic domains can for example be manufactured.

Preferably at least one further polymer and/or particle layer can be applied on the hydrophilic polymer layer. This lies on the brush-like structure like a porous film.

As hydrophilic polymers can preferably be used polysaccharides, polyalcohols, polyethers, polyamides, polycarboxylic acids, polysulfates/sulfonates, poly-phosphates/—phosphonates and/or combinations of these, which can be further chemically functionalized by subsequent modification steps.

Such groups include for example isothiocyanates, isocyanates, carboxylic acid azides, N-hydroxysuccinimides, N-acylimidazoles, sulfonylchloride derivatives, aldehyde, keto, glyoxal, oxirane, carbonate, arylhalogenide, imidoesters, anhydrides, halogenalkyls, halogenacyls, maleimides, aziridines, acryloyls, sulfhydryls, disulfides, diazoalkanes, diazoacetyls, imidazolylcarbamates, hydrazides, diazo, arylazides, benzophenones, diazopyruvates or diazirines. A favourable further embodiment represents a functionalization e.g. with nitrilotriacetic acid (NTA)derivates, so that ligands can be immobilized by means of a metal chelate. The coupling of molecules, which can immobilize ligands by a biospecific recognition reaction, is also possible.

Likewise biological effectors, e.g. growth or adhesion factors respective blood clotting-inhibiting substances, e.g. hepariri can be immobilized. Biologically active coatings are thus created, which can selectively effect in vivo certain reactions of the surrounding tissue.

By favorable further transformation of the coating according to invention the polymer adhesion mediator layer is arranged parallel to the substrate surface, which causes a good adhesion of the polymer chains on the substrate as well as a high density of functional groups available for coupling.

Structure and immobilization capacity of the hydrogel structures according to the invention can be controlled by variation of the adsorption and coupling conditions. Apart from decrease of the concentration of the second polymer, which leads to loop and train structures, changes of pH and salt concentration during adsorption of the adhesion mediator polymer, a nano-rough underlayer can be created, on which, as described above, a second polymer layer can be applied in brush-conformation.

They possess a higher immobilization capacity due to their increased surface than planar structures, without exhibiting a diffusion limitation which is characteristic for thicker hydrogels.

A further possibility of achieving nano-rough surfaces is the use of particles and/or globular proteins as adhesion mediators.

In a further favorable embodiment amphiphilic polymers or polyamines can be used as polymeric adhesion mediator layer as well.

In this application said amphiphilic polymers can carry disulfide, sulfide, diselenide, selenide, thiol, isonitrile, nitro-, selenol, trivalent phosphorus (P III)containing, isothiocyanate, xanthate, thiocarbamate, phosphine thioacetate or dithioacetate groups.

The coatings according to the invention can be combined with different substrates. For electro-chemical applications the use of conductive substrate materials is favored. The layers are also electro-chemically of limited permeability for ions. This leads to the fact that application of a potential to an underlying metal substrate make it possible under certain conditions to deposit biomolecules selectively and reversibly in the brush-like polymer layer. If one immobilizes enzymes in the polymer layer, one receives an extremely fast responding enzyme sensor when using a suitable potential.

Likewise, a substrate like glass and/or different oxidic material can be used, whereby this can be silanized by an additional reaction step.

A substrate coating is also possible when using noble metals, e.g. Ag, Au, Pt or Pd. The adhesion mediator layer can be applied here both directly on the substrate surface, or be coupled by a bisfunctional alkylmercaptane.

The coating of substrates which are based on plastic materials can be done according to the invention, whereby the plastic substrates can additionally be functionalized before the coating through treatment with oxidizing agents, by the use of surface-modifying plasma methods or ionizing radiation. Another advantageous embodiment includes coating of hydrophobic surfaces having a sufficiently low surface energy with an adhesion mediator layer consisting of amphiphilic polymers.

A further substrate alternative to be coated according to invention, can be natural or artificial fibers or a combination of both.

The adsorption of the adhesion promoting polymer as well as the covalent coupling of the brush-like arranged second polymer layer can be easily done from aqueous solutions. As the assembly of the structure of this layer element takes place via self organization respectively under complete conversion of the functional groups, the manufacturing process according to the invention possesses a system-inherent high error tolerance, which leads to constant layer qualities.

Preferably the coatings have a thickness between 10 and 500 nm and especially preferred between 10 and 100 nm.

These applications include the immobilization of ligands in an affinity sensor or the immobilization of enzymes in amperometric enzyme sensors. In addition, a selectivity increase of sensors is achieved, as molecules above a certain molecular weight can be excluded, whereby the threshold can be adjusted by means of the structure of the coating.

The layers according to the invention can be used particularly favorably for the coating of biochips, here particularly protein chips, since they suppress nonspecific binding to the chip surface on the one hand and on the other side ensure a high immobilizatioin capacity.

In mass spectrometry, in particular for MALDI (Matrix Assisted Laser Desorption Ionization), the aforementioned hydrogel layers can not only be used to concentrate the biomolecules to be analyzed on the target surface by electrostatic adsorption, but also to investigate biospecific interactions with the covalently immobilized ligands.

Conventionally coated MALDI targets, as described for example in Wo 98/59360, are only badly suitable for this because of the small immobilization capacity of the planar coated surfaces and the resulting signal/noise ratio of the measurements made herewith is too small.

The same applies to hydrogel surfaces, which are manufactured in accordance with the method described in U.S. Pat. No. 5,436,161, since these, besides having the disadvantages already described above, lead to hydrogels with a much to small immobilization capacity.

In contrast, hydrogel layers with a immobilization capacity several times higher can be manufactured with the procedure according to the invention. The biomolecules adsorbed to these layers yield a very good signal quality in the following MALDI analysis. Since the aforementioned electrostatic concentration in the hydrogel matrix can only occur if the biomolecules carry an opposite charge than the hydrogel, and the charge of the biomolecules is again dependent on their pI (isoelectric point) and the pH of the sample solution, the layers according to invention can be used to determine the pI of unknown biomolecules, if required also in mixtures. For this purpose the unknown sample is dissolved in buffers with different pH's and the solution then applied onto hydrogel coated substrates. Since only those molecules will be accumulated in the negatively charged hydrogel matrix, whose pI's is higher than the adjusted pH's of the sample buffers, suitable gradation of the pH gradients and subsequent quantification of the adsorbed biomolecules by MALDI analysis or another method suited to quantify adsorbed biomolecules makes it possible to determine the pI of the individual components of a mixture quite exactly.

In a further embodiment the hydrogel layers can be used for the sequence analysis of biomolecules, in particular by proteins. First one immobilizes a suitable, e.g. proteolytically acting enzyme in the hydrogel matrix and in a subsequent step adsorbs the biomolecules to be analyzed. The masses of the resulting products of decomposition can then be determined by means of MALDI.

Through the use of a suitable polymer adhesion mediator it is in a further embodiment possible to integrate UV absorbing substances e.g. 3,5-dimethoxy-4-hydroxycinnamic acid, usually drop deposited directly before the MALDI measurements, by covalent coupling into the adhesion mediator.

The energy-adsorbing effect of the UV absorber is thereby not only distributed more evenly over the target surface, a possible denaturation of the examined bio molecules is also prevented, since these do not come into contact with the UV adsorbent. A larger quantity of UV absorbing material can be applied onto the surface, by encapsulating these substances in particles, vesicles or liposomes and using these as adhesion mediators.

It is possible, when using conductive substrates, to use the coatings for the immobilization of biomolecules by application of a potential in a further variant also for the stationary chromatography. Here a stationary phase with variable adsorptive properties can be realized by variation of the potential applied.

On the other hand it is possible to use the layers according to the invention for the optimization of chromatographic processes or for the characterization of unknown quantities of substance mixtures. For this one immobilizes several layers with different adsorptive properties next to each other on a carrier.

This could be, for example, differently loaded, hydrophobically derivatized hydrogel layers with metal ions or with chelating groups. If a solution with a substance which is to be examined is added onto such a carrier and the quantity adsorbed to the different layers analyzed with a suitable analysis method, e.g. MALDI or SPR, then substance-specific adsorption profiles can be created very fast.

These can then be used for example, in order to develop and/or optimize chromatographic purification processes. If one subjects such a carrier with an unknown sample mixture, then the single components are adsorbed depending on their respective affinity in different quantity to the different layers.

The resulting specific adsorption pattern can be determined by subsequent MALDI analysis.

Wide ranges of applications also exist in the employment as dirt-deflecting coatings or non-adhesive coatings in aqueous media. These include the coating of filling materials of bioreactors, just as the bioinert coating of medical instruments or also implants, which are in contact with body fluids and/or tissues. Of particular interest for the latter applications is the possibility to derivatize the coatings with other biomolecules. Thus tissue-specific adhesion or growth factors can for example be immobilized into the coatings. This can induce and/or accelerate e.g. desired subsequent growth around implants. If one immobilizes blood clotting suppressing biomolecules, e.g. heparin to the coatings, then the hemocompatibility is improved substantially. Compared to conventional methods for the immobilization of heparine this method has the advantage, that thicker and more stable layers can be realized with reduced heparin consumption.

A further variant represents the coupling of pharmaceutically active substances with the adhesion mediator or hydrogel layer. If these are coupled for example over hydrolyzeable bonds, e.g. ester functionalities, they are delivered by gradual hydrolysis slowly into the environment. FromTL this results a favorable possibility for the controlled release of active substances.

A further application lies in the coating of nano and micro particles. These can be stabilized as well as bioinertisized very well by the coatings according to the invention against adsorption and flocculation. In addition the coating represents an excellent matrix for the immobilization of bio- and other molecules. Biofunctionalized particles of this kind can be used both for analytic and preparative purposes, and— with the meaning of the previous paragraphs—as a tissue specific active substance carrier, which binds itself for example using specifically binding antibodies to disease tissue, there slowly releasing pharmaceutically active substances.

For optical elements the coating can be used as anti-fog coating just as also for the retention of liquids. The latter being a highly desired characteristic for the surface of contact lenses. Since the hydrogel layers in addition have a lubricating effect in aqueous media, the wearing comfort of such coated lenses is significantly increased.

DETAILED DESCRIPTION

Various embodiments and implementations of the coating according to the invention are presented in the following schematic figures and examples.

Figure 1:
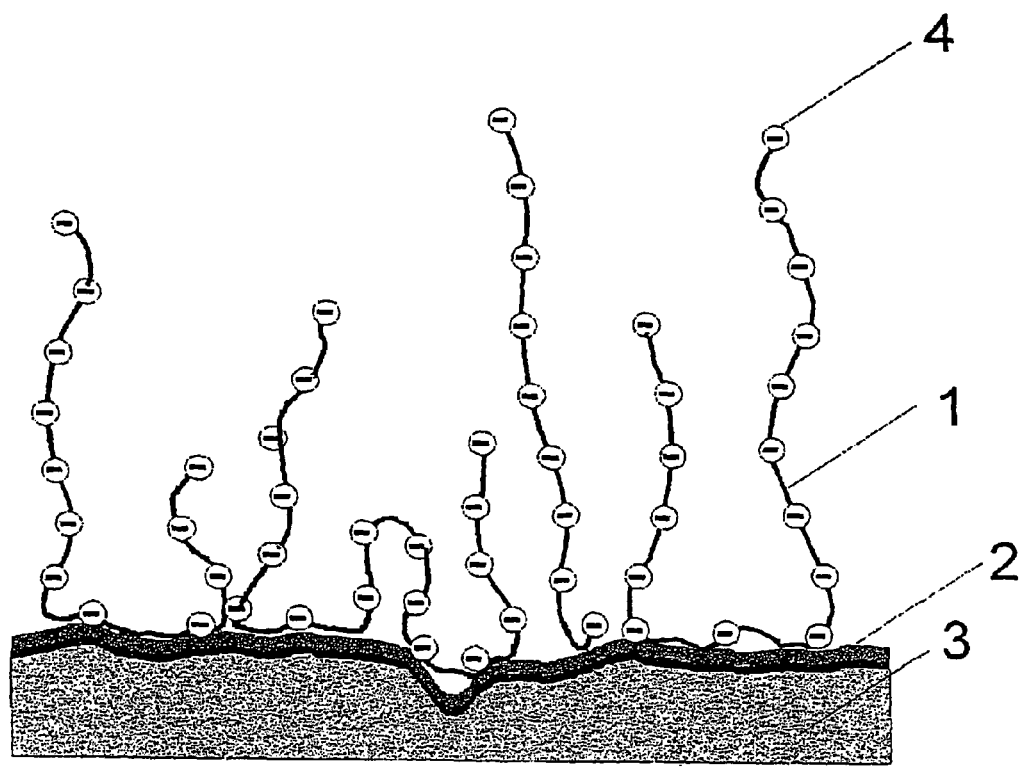
FIG. 1 shows schematically the structure of a coating according to the invention.

FIG. 1 shows schematically the structure of a coating according to the invention. The substrate designated here (3) is covered with a polymer adhesion promoting layer (2), whereby their polymer chains are arranged parallel to the substrate surface, so that a high density of functional groups is present, which is suitable for the further coupling of the hydrophilic polymer (1).

The hydrophilic polymer (1) is thereby arranged vertically to the substrate surface, so that a multiplicity of functional groups (4) is available for the immobilization of biomolecules.

Figure 2:
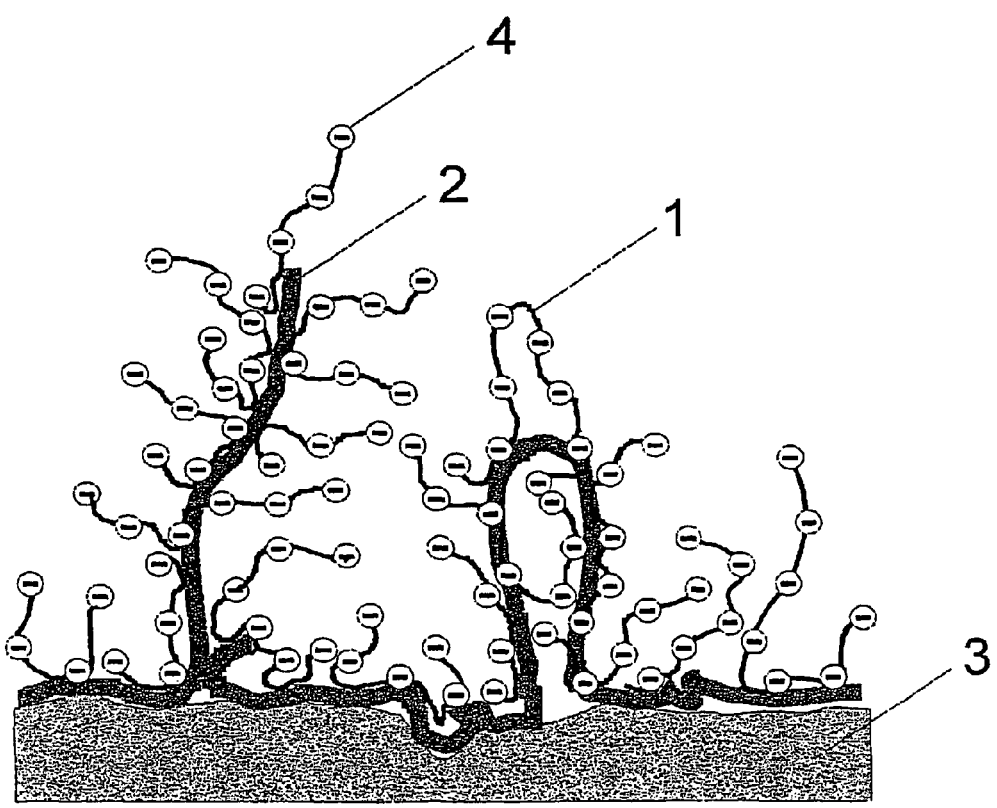
FIG. 2 shows schematically the structure of a coating according to the invention on a surface roughened up in the nanoscale and/or microscale.

FIG. 2 shows schematically the structure of a coating according to the invention on a surface roughened up in the nanoscale and/or microscale. These fractal structures form if the concentration of the adhesion mediator is increased, so that the adhesion promotor layer does not align itself completely parallel to the substrate surface, but also partly loop-like away from the substrate.

An increased immobilization capacity can be achieved in relation to the planar structure represented in FIG. 1 due to the increased surface area. A further advantage is that diffusion limitation typically occurring when using hydrophilic polymers of higher molecular weight can be avoided.

Figure 3:
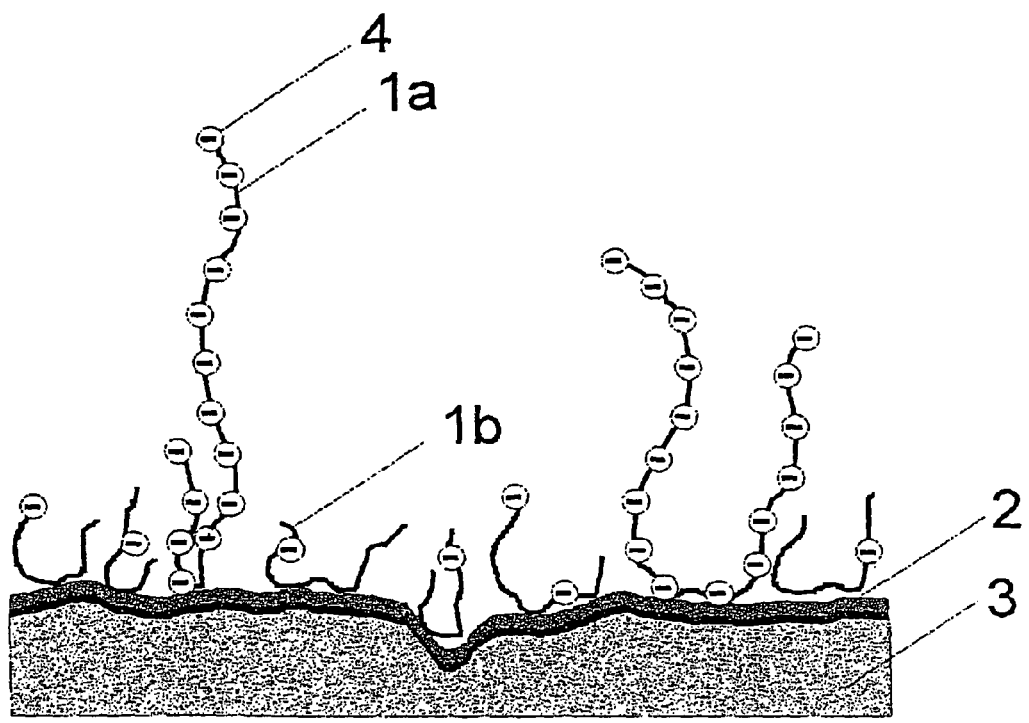
FIG. 3 shows schematically the mixed coverage of the substrate with hydrophilic polymers of different molecular weight and charge densities.

In FIG. 3 the mixed coverage of the substrate with hydrophilic polymers of different molecular weight and charge densities is schematically shown. (1a) is a polymer with a higher molecular weight and a higher density of negatively charged functional groups (4) as polymer (1b). Both polymers can be coated in one processing step via an adhesion promotor (2) onto any substrate (3).

Advantages of such structures lie in the adjustable spatial distance between the high-molecular chains through the mixing proportion (1a) to (1b), leading to the development of a hydrogel with adjustable pore size. This can be used favorably for the increase of the selectivity of sensors. If polymers of different charge densities are mixed and ligands coupled preferentially to the high-loaded chains in a second processing step, then the lowered charge of the intermediate area can lead to clearly reduced nonspecific interactions.

Figure 4:
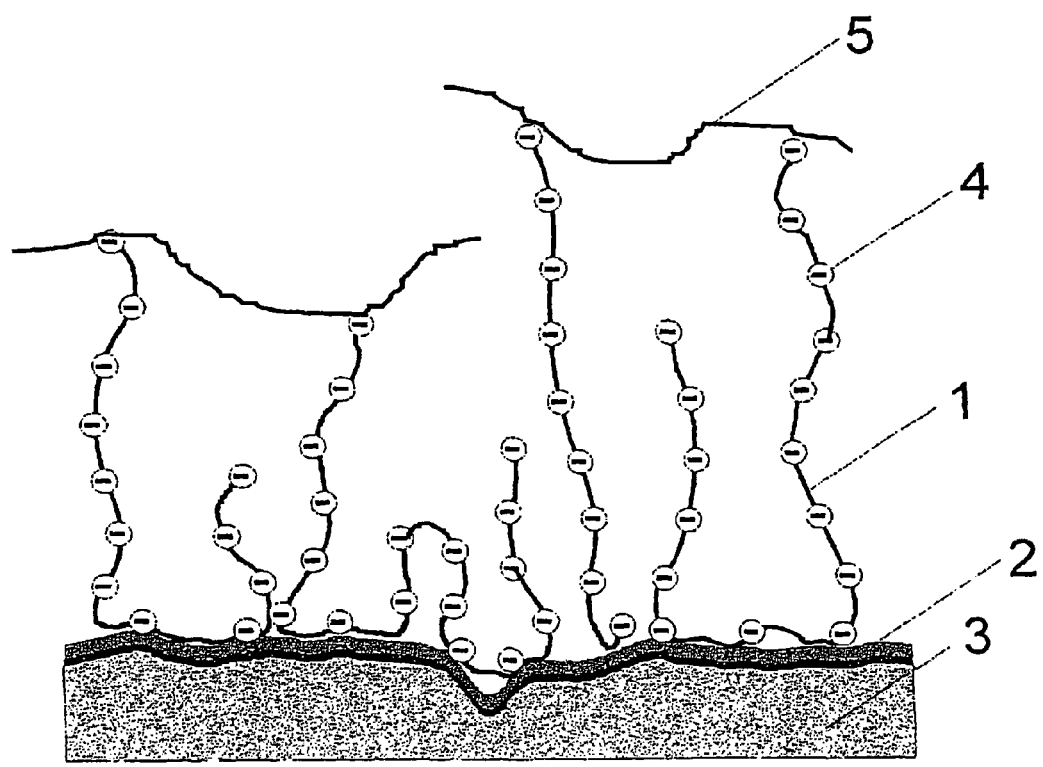
FIG. 4 shows schematically a layer element similar to FIG. 1, in which another, preferentially uncharged indifferent polymer layer in train configuration is applied onto the hydrophilic polymer layer in brush-conformation.

FIG. 4 shows schematically a layer element similar to FIG. 1, in which another, preferentially uncharged indifferent polymer layer (5) in train configuration was applied onto the hydrophilic polymer layer in brush-conformation (4). Such architectures represent after immobilization of a ligand within layer (4) a diffusion-limited coating, which is suitable particularly favorably for concentration determination of analytes with affinity sensors. Furthermore, the layer (5) shields the actual sensitive layer (4) against nonspecific interactions from the sample matrix and can likewise be used as a molecular filter.

EXAMPLE 1

Carboxymethyl (CM) Dextran with Reduced Degree of Carboxymethylation.

To a solution of 0,5 g dextran MW 60 kDa (Sigma) in 10 ml 3 M NaOH are added under constant stirring 0.74 g iodine acetic acid. After 70 min at ambient temperature the reaction mixture is neutralized with phosphoric acid and dialyzed against destined water. The carboxymethyldextran solution is then concentrated to 1-2 ml, 5 ml methanol are added and the CM dextran afterwards precipitated with 25 ml ethanol. After centrifugation, washing twice with ethanol and drying under vacuum, 410 mg of a white powder are obtained. The degree of carboxymethylation, which can be determined for example by titration of an aliquot converted into the free acid by means of acidic ion exchangers, amounts to 1 COOH group per six anhydroglucose units.

EXAMPLE 2

CM Dextran Monolayer on Carboxylfunctionalized Surfaces 1 mm thick glass chips, with one side vapor deposited gold coated are cleaned, covered with a solution of 0.1% poly (ethylene-co-maleinic acid co-maleinic acid mono (carboxymethylethylsulfide) ester) in water and shaken for 1 h. The thus carboxylfunctionalized glasplates are converted into the active NHS ester by an one hour treatment with 20 mM N-(3-dimethylaminopropyl)-N'-ethylcarbodiimide (Fluka) und 10 mM N-hydroxysuccinimide (Merck) in 0,1 M sodium 2-morpholino-ethanesulfonatebuffer, pH 6,0 (Fluka). The dried substrate is covered with a few µl of a solution of 20% ⅙ CM dextran MW 60 kDa (from example 1), 2% glucuronic acid and 1% dimethylaminopyridine (Merck), after removing the solvent in vacuum, it is incubated 10 min at 50° C. Not bound dextran is dissolved by a 5 min application of 0.1 M HCl.

EXAMPLE 3

CM Dextran Monolayer on Aminofunctionalized Surfaces 1 mm thick glass chips, with one side vapor deposited gold coated are cleaned, covered with a solution of 5% polyethylenimine MW 600-1000 kDa (Fluka) in water and shaken for 15 min. After washing with destilled water the aminofunctionalized dried substrate is covered with a solution of 15% ⅙ CM dextran MW 60.000 kDa (from example 1), incubated for 1 h with each 0,1 M of N-(3-Dimethylaminopropyl)-N'-ethylcarbodiimide (Fluka), N-Hydroxysuccinimide (Merck) und sodium phosphate, pH 6,0, (Fluka). The non-covalently bound gel-like solidified CM dextran is removed with 0.1 M sodium carbonate buffer pH 9.4 over 10-20 h. The remaining monolayer exhibits a contact angle of below 5°.

EXAMPLE 4

Figure 5:
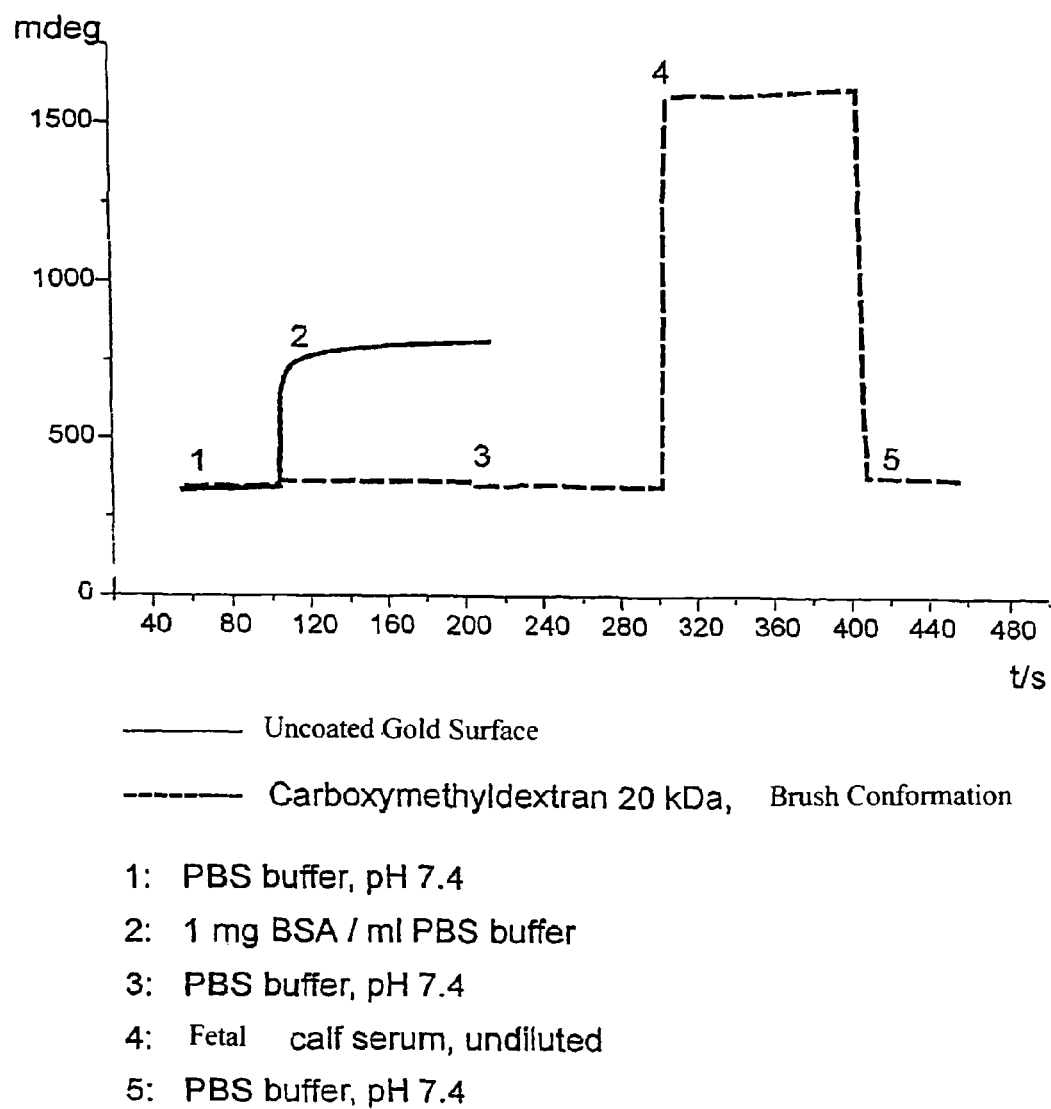
FIG. 5 is a diagram showing stabilization against nonspecific protein adsorption by CM dextran coatings.

Stabilization against Nonspecific Protein Adsorption by CM dextran coatings (FIG. 5)

The gold-coated, CM dextran modified glass substrate from example 2 is examined for nonspecific interactions in a surface plasmon resonance (SPR) biosensor (IBIS, XanTec) by installing it in the device and by application of different protein-containing solutions. To an uncoated reference spot approx. 5 ng protein/mm$^2$ are adsorbed irreversibly already from a solution of 1 mg bovine serum albumine (BSA)/ml PBS buffer pH 7.4 within a short time, which corresponds to an almost complete coverage. An adsorption to surfaces covered with carboxymethyldextran does not occur even when using undiluted fetal calf serum.

EXAMPLE 5

Figure 6:
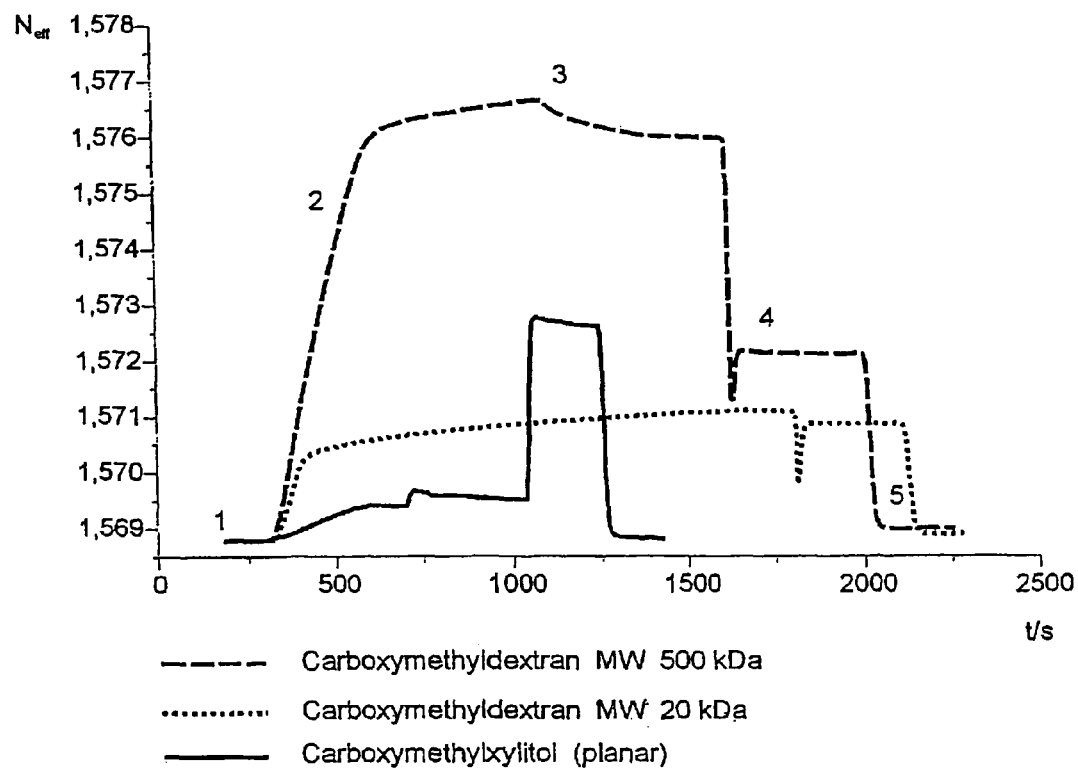
FIG. 6 is a diagram showing the increase of the immobilization capacity by three-dimensional hydrogel structures.

Increase of the Immobilization Capacity by Three-Dimensional hydrogel structures (FIG. 6)

A gold coated glass substrate with a carboxymethyldextran MW 500 kDa coating analoguos to example 3 is installed in a surface plasmon resonance (SPR) bibsensor (IBIS, XanTec) and the immobilisation capacity of the sensor surface is measured. The application of a solution of 50 µg BSA/ml 10 mM sodium acetate buffer pH 5,0 yields an electrostatic adsorption approx. five times higher in relation to an accordingly carboxylated planar surface. In the presented example, the concentrated BSA is again quantitatively desorbed using an elution buffer(2 M NaCl, pH 13). By converting a fraction of the carboxyl groups into active NHS esters by addition of 20 mM N-(3-dimethylaminopropyl)-N'-ethylcarbodiimide (Fluka) and 10 mM N-hydroxysuccinimide (Merck) in 0,1 M sodium 2-morpholino-ethanesulfonate buffer, pH 6,0 (Fluka), the first electrostatically adsorbed proteins will be covalently coupled and cannot be eluted anymore.

EXAMPLE 6

Three-Dimensional Fractal Hydrogel Structures

The gold sensordiscs are coated in accordance with example 3 with carboxymethyldextran. Instead of polyethylenimin, polyallylamine (Aldrich No. 28.3223) high molecular weight and instead of ⅙ CM dextran MW 60 kDa this time fully carboxylated CM dextran MW 5 kDa are used. A fraction of the batch is washed with 2 M NaCl, 10 mM NaOH and another fraction with 2 M NaCl, 10 mM HCl Using the acidic solution, the immobilization capacity is approx. 8.5 ng BSA/mm$^2$; using the alkaline elution only 5,3 ng BSA/mm$^2$. This can be ascribed to the loose, partly unbound structure of the polyallylamine chains after the acidic elution, which creates a larger surface and thus a higher immobilisation capacity.

EXAMPLE 7

Mixed Hydrogel-Layers

The gold sensordiscs are coated in accordance with example 3 with carboxymethyl dextran, whereby a mixture of 7,5% ⅙ CM dextran MW 5,000 and 7.5% fully carboxylated dextran MW 60,000 is this time used instead of ⅙ CM dextran MW 60,000.

The resulting coatings show a clearly smaller diffusion limitation concerning the binding of bio molecules to immobilized ligands as well as improved stabilization against non-specific interactions.

EXAMPLE 8

Figure 11:
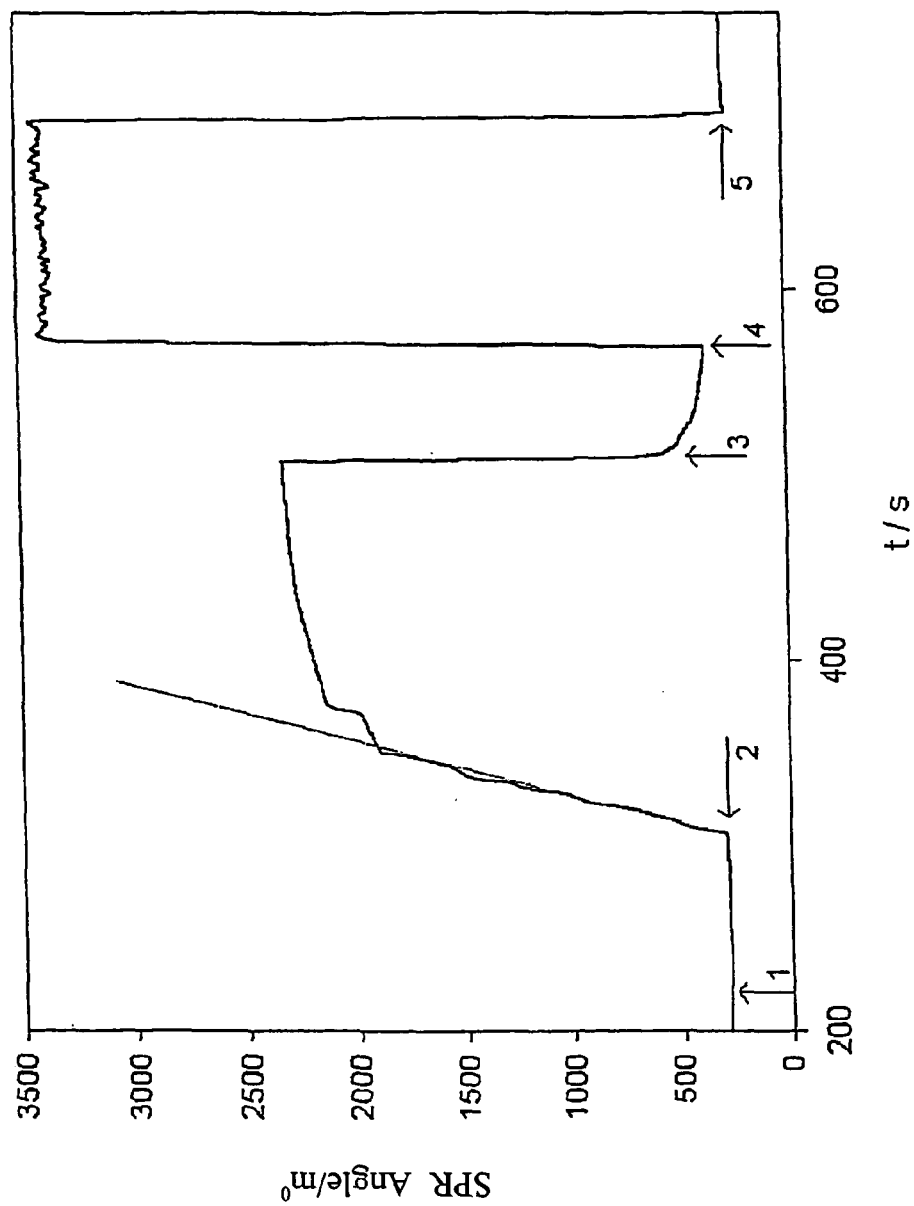
FIG. 11 is a graph showing diffusion-limited hydrogel structures.

Diffusion-Limited Hydrogel Structures (FIG. 11)

The gold sensordiscs are coated in accordance with example 3 with carboxymethyl dextran. Subsequently, the carboxylgroups are again activated with 0.2 M of N-(3-Dimethylaminopropyl)-N'-ethylcarbodiimide and N-hydroxysuccinimide each and the chips are incubated in a solution of 10% dextran MW 500,000 in 0,1 M PBS buffer pH 7,5. After a reaction time of 2 to 4 hours unbound dextran is washed off with 0,1 M sodium carbonate buffer pH 9.4 for 4 hours. The resulting doublelayers show a clearly higher diffusion limitation concerning the binding of bio molecules to immobilized ligands than the mono layers described in example 3.

They are therefore preferably suitable for concentration determinations. FIG. 11 shows the electrostatic adsorption of BSA into this double layer structure. The linear, diffusion-controlled range is marked by arrows.

EXAMPLE 9

Figure 7:
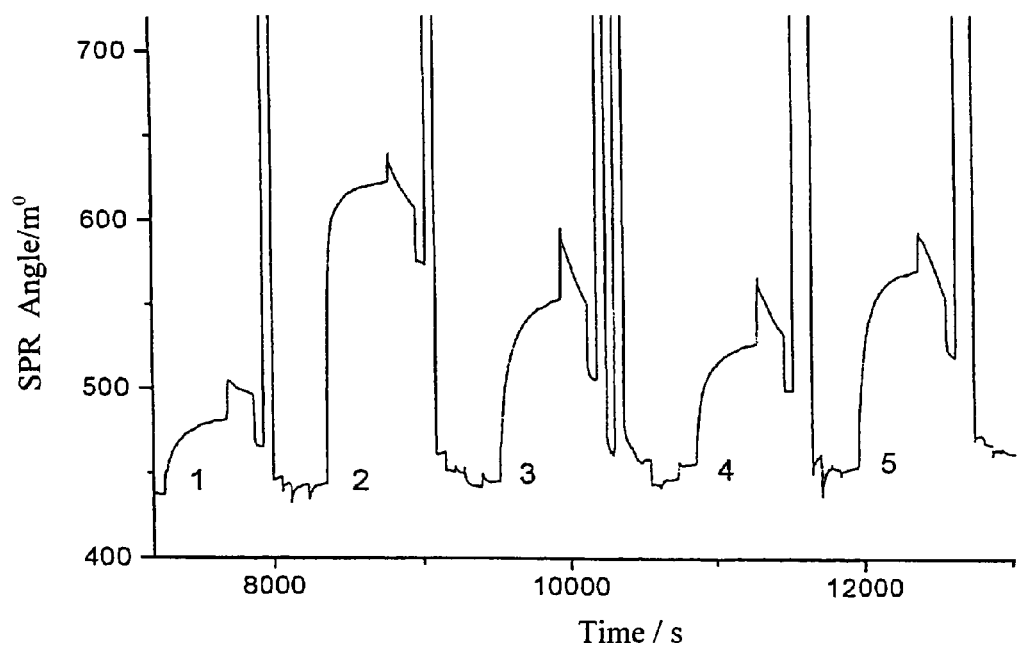
FIG. 7 is a diagram showing reversible antibody binding to immobilized Haptene.

Reversible Antibody Binding to Immobilized Haptene (FIG. 7)

In order to test the suitability of the hydogel structures described in the above examples as immobilization matrices for immunoassays, 2,4-dichlorophenoxyacetic acid-3-aminopropylamide was covalently coupled to a SPR sensor chip derivatized with CM dextran. The haptene modified surface is then subjected to anti-(2,4 dichlorophenoxyacetic acid) anti-bodies with concentrations of 1 Fg/ml (1), 16 µg/ml (2), 2 µg/ml (3), 1,5 µg/ml (4) and 3 µg/ml (5). The antibodies were dissolved in PBS buffer, pH 7.4; after the antibody addition the dissociation was measured using a solution of 100 µg 2.4 dichlorophenoxyaceticacid-3-aminopropylamid/ml PBS buffer and the chip surface afterwards completely regenerated with 0,5 M NaOH.

In each cycle the baseline signal was readjusted with PBS buffer before the next assay. After each assay the bound antibodies were removed with denaturing regeneration solution almost quantitatively.

EXAMPLE 10

Figure 8:
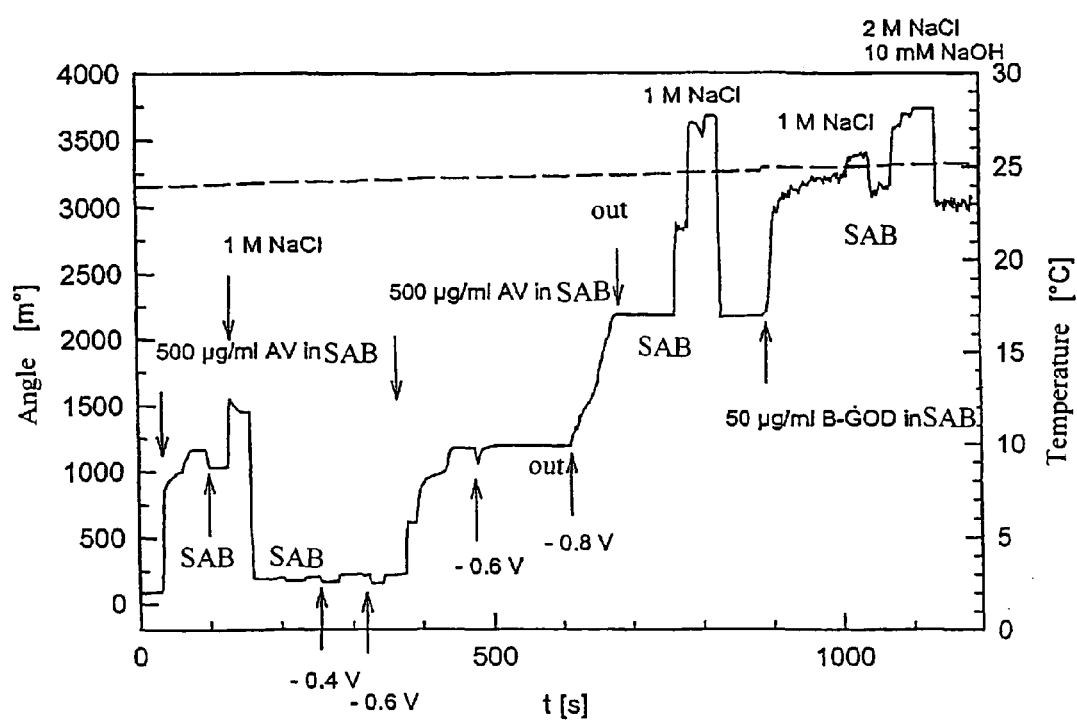
FIG. 8 is a diagram showing electrodeposition in carboxymethyldextran hydrogel layers.

Electrodeposition in Carboxymethyldextran Hydrogel Layers (FIG. 8)

FIG. 8 shows the irreversible binding of avidin to dextran covered sensor surfaces by creation of a sufficiently negative potential under conditions, at which no adsorption would take place without any applied potential. First, the surface is regenerated by treatment with 1 M NaCl (100 seconds). As control a negative potential of –0,4 and –0,6 V (at approx. 300 seconds) in absence of avidin is applied afterwards, whereby no change of the SPR signal is observed. After 400 seconds first 500 µg avidin/ml 2 mM sodium acetate buffer pH 4.7 is added, after which approx. 8 ng/mM$^2$ are adsorbed. Additional avidin is adsorbed by application of different negative potentials (at 600 seconds). As an elution experiment by treating the surface with 1 M NaCl (at 800 seconds) shows, the protein remains irreversibly in the matrix. Avidin is biologically fully active, which is demonstrated by binding of biotinylated glucose oxidase (at 900 seconds). The interaction is stable against elution with 10 mM NaOH in 2 M NaCl.

EXAMPLE 11

Figure 9:
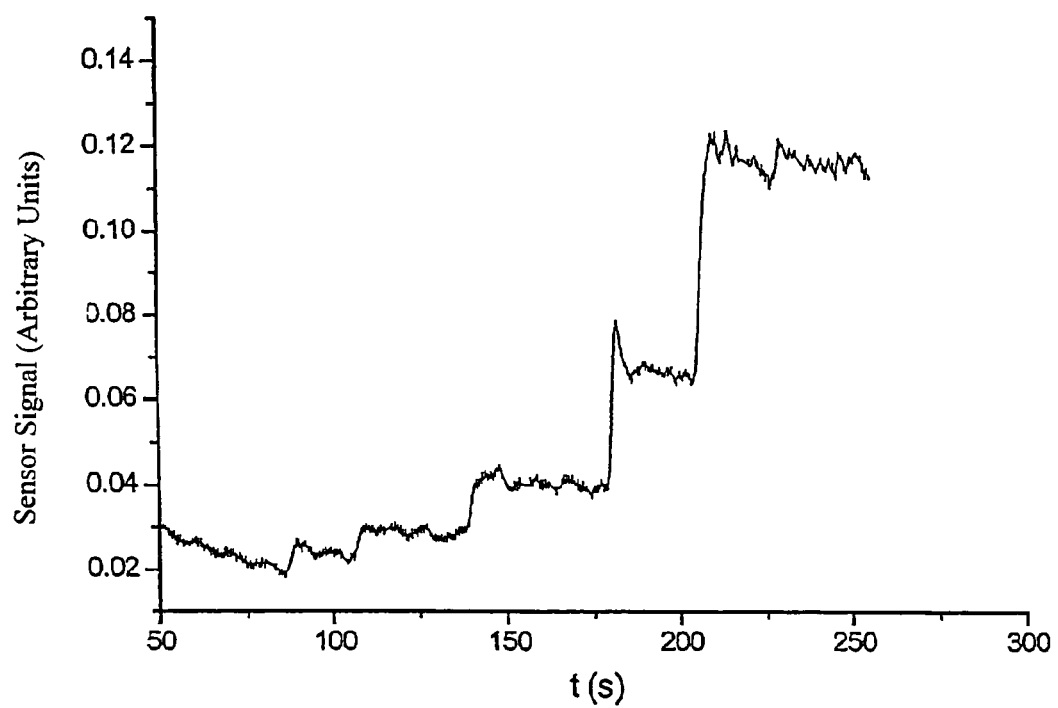
FIGS. 9 and 10 are graphs showing the production of ulra thin enzyme layers as well as use in an enzyme sensor.

Production of Ultra Thin Enzyme Layers as well as use in an Enzyme Sensor (FIG. 9, 10)

Figure 10:
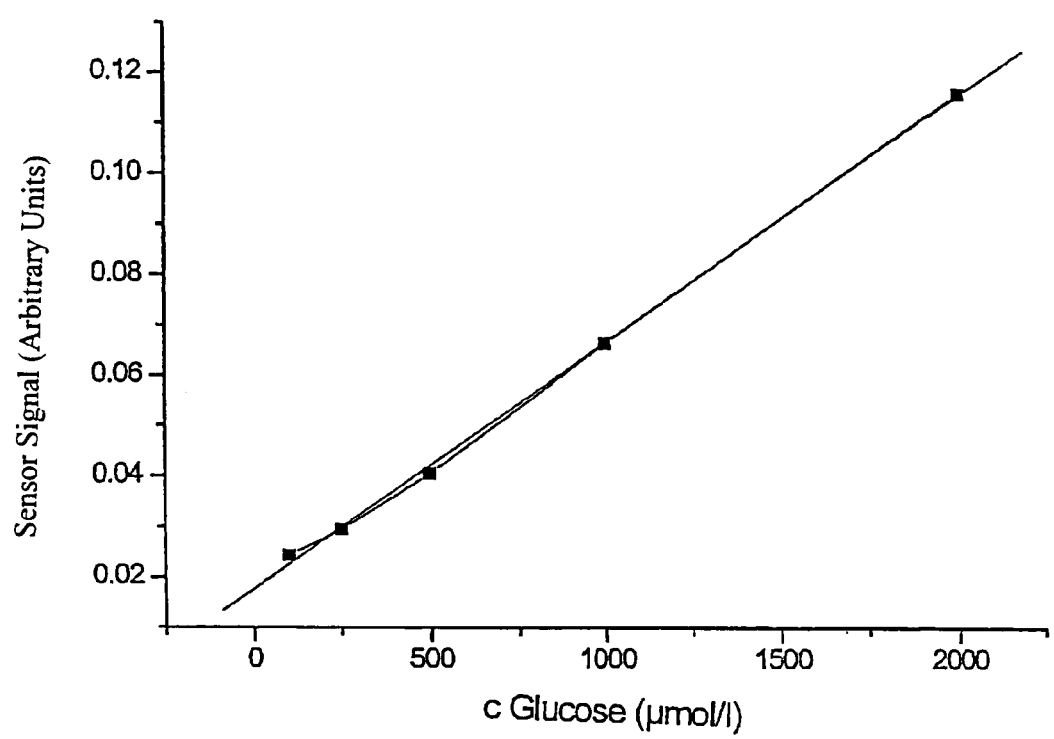

FIG. 9 exemplarily shows the determination of glucose with GOD-Pt-electrodes (GOD: glucose oxidase)on the basis of carboxymethyl dextran monolayers. The Pt-electrodes, measuring 800×800 µm are first covered in accordance with example 3 with a mono layer ⅙ CM dextran of 60 kDa on PET adhesion promotor. Avidin is deposited from a solution of 500 µg/ml avidin in 2 mM sodium acetate, pH 4,7 in accordance with example 8 by application of a potential of –0,8 V (1 h) to the electrode surface. Subsequently, one incubates with biotinylated glucose oxidase (50 µg/ml) in PBS buffer, pH 7.4 over 1 hour. The electrodes derivatized in such a way are calibrated with differently concentrated glucose solutions (100, 250, 500, 1000 and 2000 µmol/l Glc) in PBS buffer, pH 7,4 (see FIG. 10). The enzymatically generated $H_2O_2$ is hereby measured at +700 mV against an Ag/AgCl reference electrode (3 M KCl).

EXAMPLE 12 (FIG. 12, 13)

Improvement of the Signal Quality of MALDI Measurements by Concentration of the Analyte Molecules in Hydrogel Layers.

Production of the reference target: A vapor-deposited gold coated MALDI target (Micromass Ltd., Manchester, GB) is cleaned and subjected 2 h to a solution of 0.5% 1-dodecanthiol in ethanol. Subsequently, one washes with ethanol and water. The hydrophobic surface is afterwards subjected to a solution of 1 mg BSA/ml 0.1 M phosphate buffer pH 7,0. A mono layer BSA was adsorbed after 2 h on the hydrophobic surface. It is rinsed and dried.

Production of the hydrogel-coated target: A vapor-deposited gold coated MALDI target (Micromass Ltd., Manchester, GB) is cleaned and coated in accordance with example 3 with carboxymethyldextran MW 2 mio. Da.

The surface derivatized in such a way is subjected 1 h to a solution of 0,1 mg BSA/ml 10 mM sodium acetate buffer pH 5.0. Subsequently, the target is rinsed with the same sodium acetate buffer or water and dried.

Figure 12:
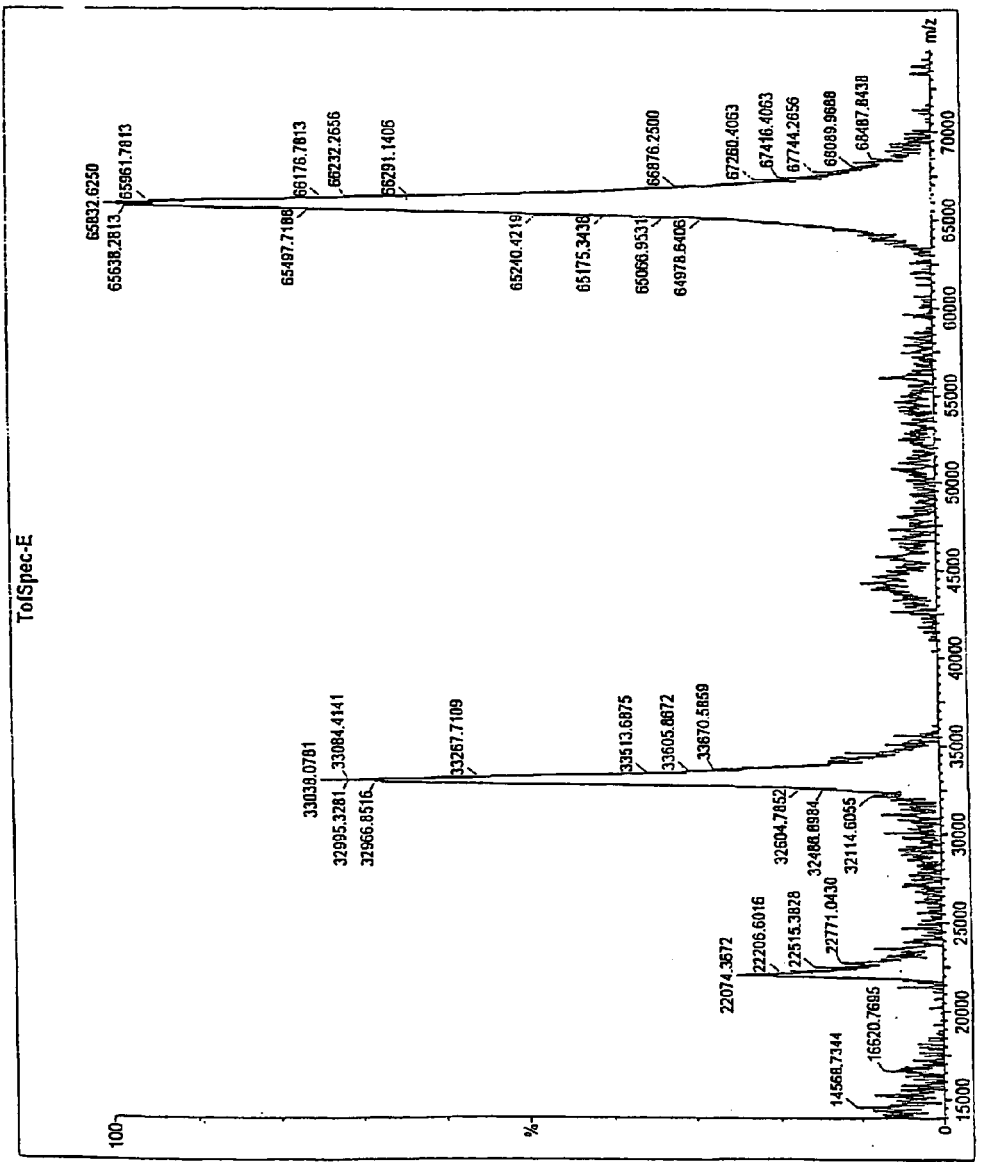
FIGS. 12 and 13 are graphs showing the improvement of the signal quality of Maldi measurements by concentration of the analyte molecular in hydrogel layers.
Figure 13:
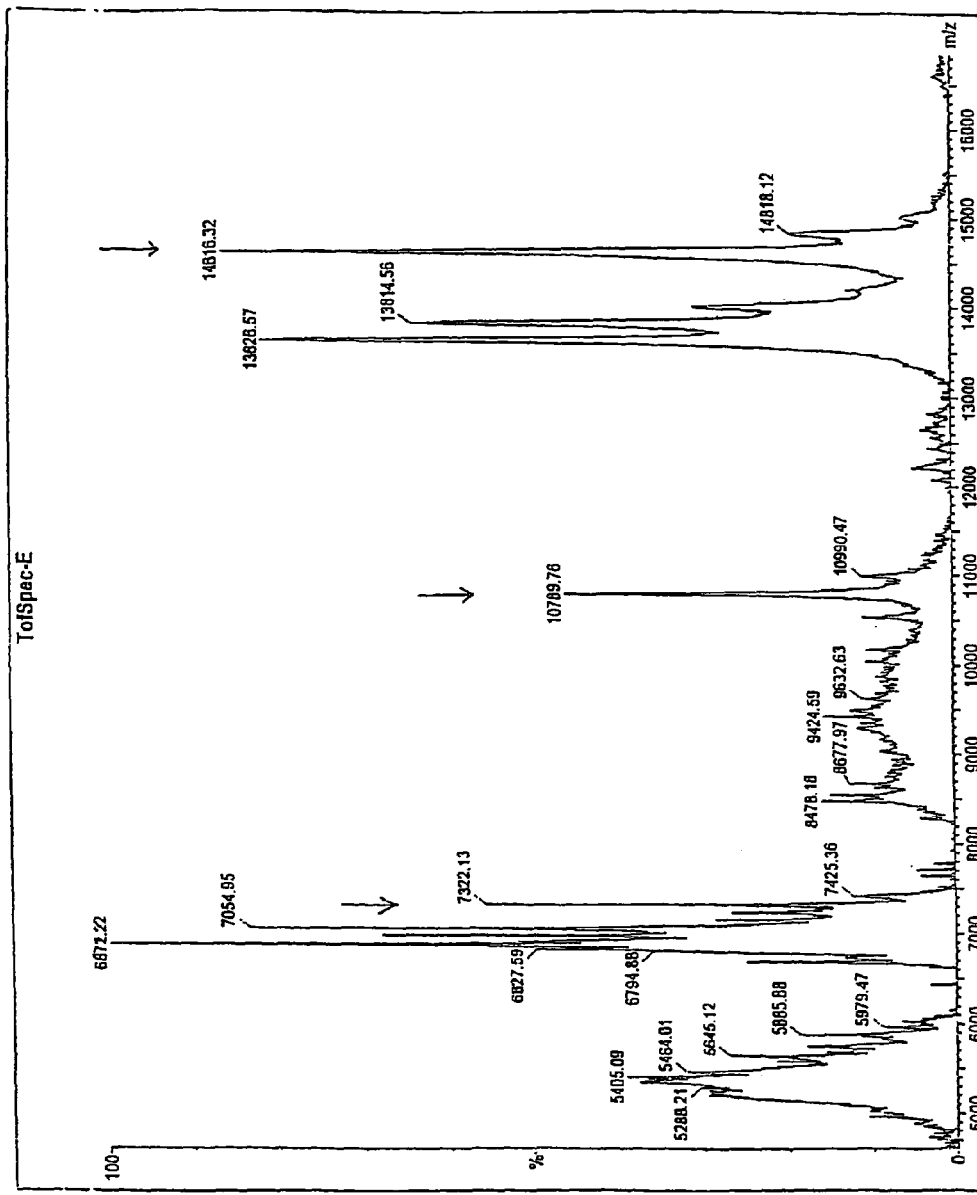

On both targets 0.5 µl 10 mg/ml sinapinic acid solution is dripped onto each measuring spot, the droplet dried and the targets then subjected to MALDI-TOF analysis. FIG. 12 shows the signal of the hydrophobic reference surface, FIG. 13 the hydrogel-coated target. The signal-to-noise ratio of the hydrogel-coated target is approx. six times better than that of the reference target.

EXAMPLE 13

Figure 14:
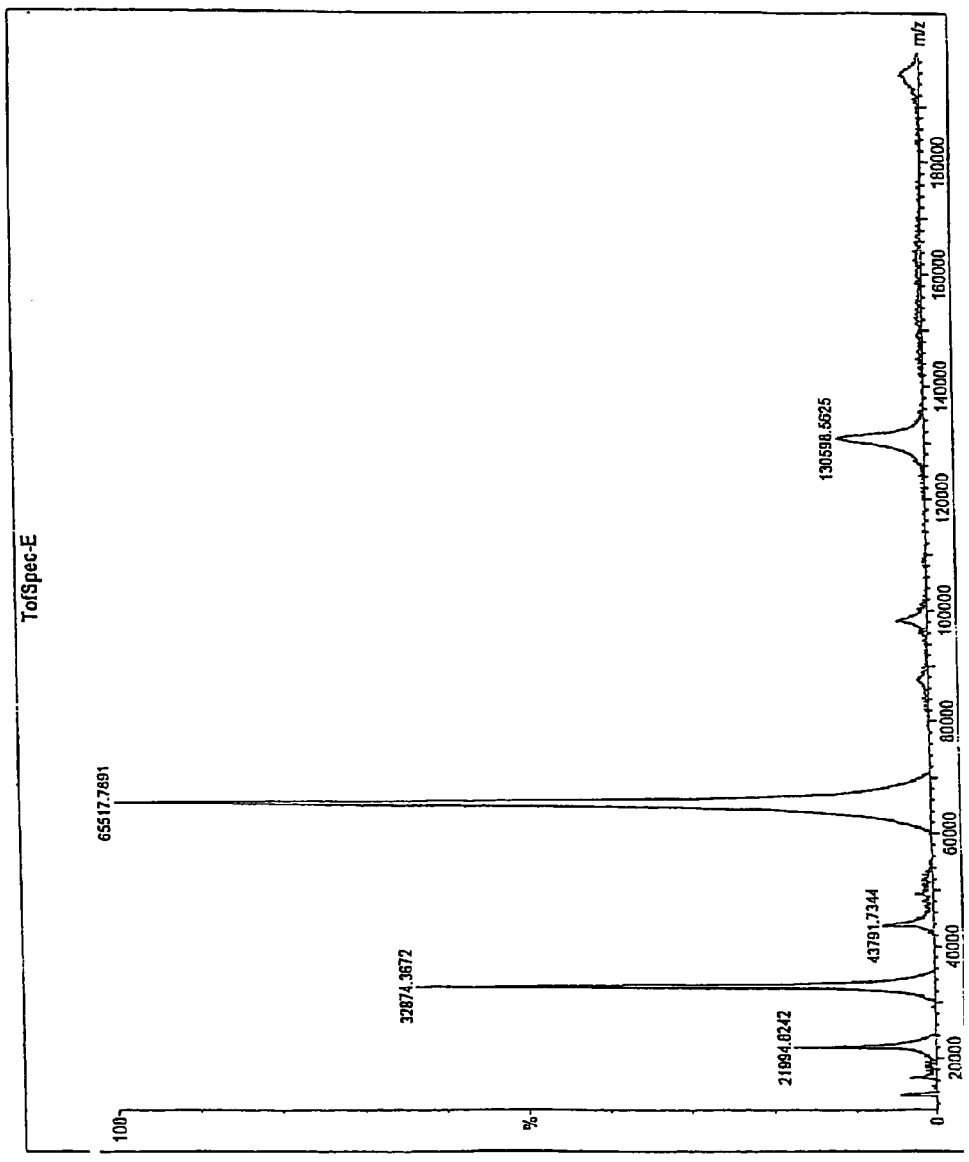
FIGS. 14 and 15 are graphs showing the separation of proteins of different pIs from cell lysates and following Maldi analysis.

Separation of Proteins of Different pIs from Cell Lysates and Following MALDI Analysis (FIG. 14, 15)

Production of the hydrogel-coated target: A vapor-deposited gold coated MALDI target (Micromass Ltd., Manchester, GB) is cleaned and coated in accordance with example 3 with carboxymethyldextran MW 2 mio. Da.

A part of the surface derivatized in such a way is subjected for 1 h to a solution of a before desalinated monocyte lysate in pH 4.8 buffer. The other part incubated 1 h with a similarly prepared monocyte lysate pH 7.3.

Figure 15:
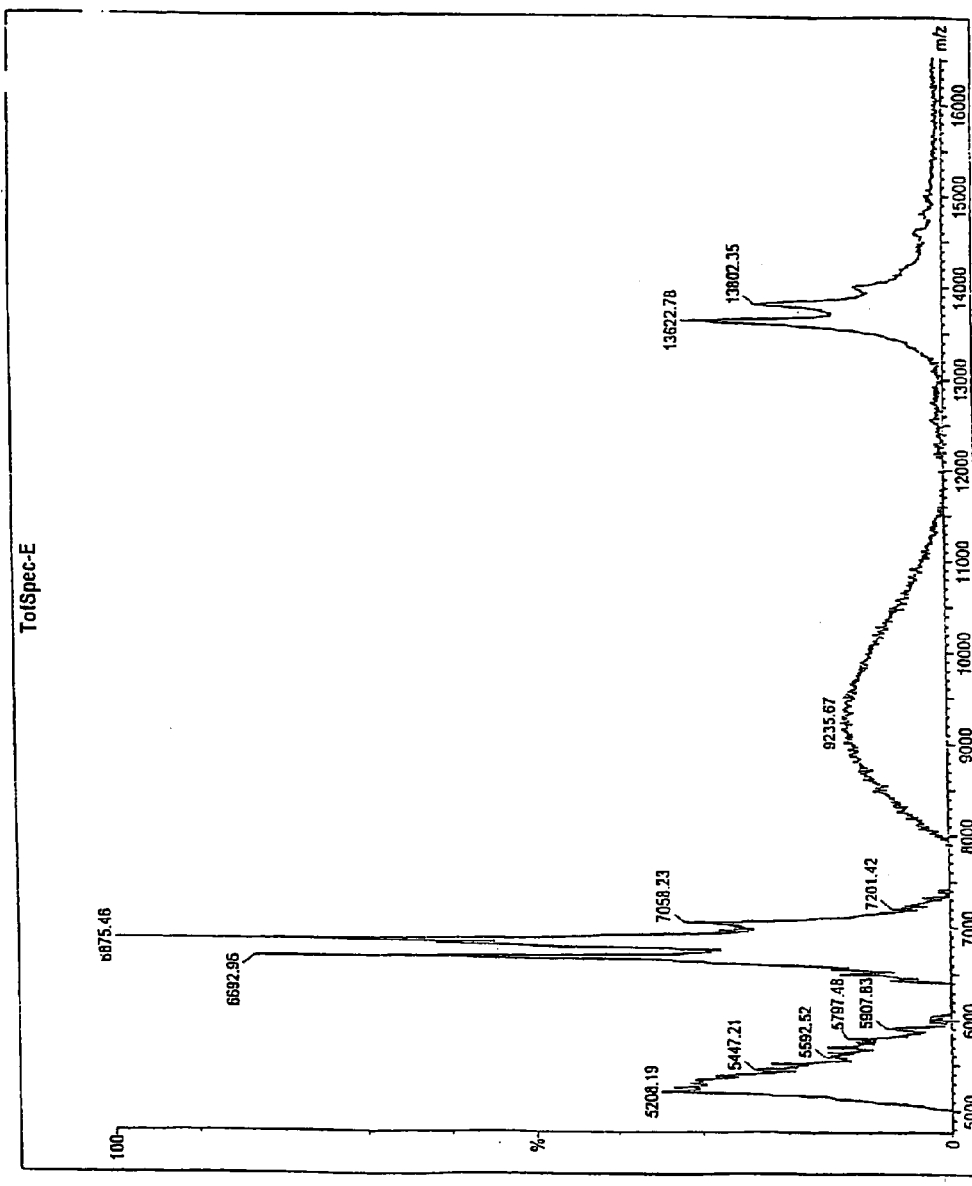

Both surfaces are rinsed with water, dried quickly and subjected in accordance with example 13 to a MALDI analysis. FIG. 14 shows the spectrum of the pH 4.8 lysate, FIG. 15 that of the pH 7.3 lysate. The arrows in FIG. 13 mark some peaks, which do not appear any more at pH 7.3. From this it can be concluded that the respective molecules have a pI between 4,8 and 7,3.

We claim

1. A coating, comprising:
   a substrate;
   a polymeric adhesion promoter covering said substrate, the covering of said polymeric adhesion promoter is such that it comprises one of: a covering parallel to the surface or a covering partly flat on the surface of the substrate, and partly loop-like covering relative to said substrate; and
   one further hydrophilic polymer layer, containing at least one polymer with a plurality of reactive groups, whose polymer chains are at least partially arranged brush-like, which is attached to said polymeric adhesion promoter, said at least one polymer of said further hydrophilic polymer layer being arranged, for the most part, vertically to said substrate, and having a plurality of functional groups attached.

2. The coating according to claim 1, further comprising: at least one further polymer- or particle-layer coupled onto said one further hydrophilic polymer layer.

3. The coating according to claim 1, wherein said further hydrophilic polymer layer is composed of at least two different polymers, which differ in their chemical composition, their charge and/or their molecular weight.

4. The coating according to claim 1, wherein said further hydrophilic polymer layer is chosen from polysaccharides, polyalcohols, polyethers, polyamides, polycarboxylates, polysulfates, polysufonates, polyphosphates, polyphosphonates and/or a combination thereof.

5. The coating according to claim 1, wherein said further hydrophilic polymer layer is further functionalized for covalent immobilization of a ligand.

6. The coating according to claim 1, wherein said further hydrophilic polymer layer is functionalized with isothiocyanate, isocyanate, azide, N-hydroxysuccinimideester, N-acylimidazole, sulfonylchloridederivative, aldehyde, keto, glyoxal, oxirane, carbonate, arylhalide, imidoester, anhydride, halogenalcyl-, halogenacyl, maleimide, aziridine, acryloyl, sulfhydryl, disulfide, diazoalkane, diazoacetyl, imidazolylcarbamate, hydrazide, diazonium, arylazide, benzophenone, diazopruvate or diazirine groups.

7. The coating according to claim 1, wherein said further hydrophilic polymer layer is further functionalized for the immobilization of ligand via a metal-chelate by e.g. reaction with nitrilotriacetic acid derivatives.

8. The coating according to claim 1, wherein molecules capable of biospecifically detecting ligands are additionally immobilised to said further hydrophilic polymer layer.

9. The coating according to claim 1, wherein biomolecules, proteins, nucleic acids, (poly-)saccharides, antibodies, adhesion factors, growth factors, coagulation-inhibiting factors like heparin and/or other biological effector molecules are immobilized to the hydrophilic polymer layer.

10. The coating according to claim 1, wherein said polymeric adhesion promoter layer consists of at least one polymer, whose polymer chains are aligned parallel to the substrate surface or of at least one globular polymer.

11. The coating according to claim 1, wherein said polymeric adhesion promoter layer is composed of particles, vesicles or liposomes.

12. The coating according to claim 1, wherein said polymeric adhesion promoter layer creates a nanoscale and/or microscale rough surface.

13. The coating according to claim 1, wherein said polymeric adhesion promoter layer consists of a amphiphilic polymer, e.g. a polyamine, that can carry disulfide, sulfide, diselenide, selenide, thiol, isonitrile, nitro, selenol, P(III), isothiocyanate, xantate, thiocarbamate, phosphine, thioacetate, silanol, silylether, silylester, silylthioester, silylthioether, or dithioacetate groups.

14. The coating according to claim 1, wherein said polymeric adhesion promoter layer carries energy absorbing groups, preferably UV absorbing groups.

15. The coating according to claim 1, wherein said polymeric adhesion promoter layer carries sinapinic acid, sinapinic acidamide, dimethoxyhydroxysinapinic acid, sinapinic acidbromide, dihydroxybenzoic acid and/or cyanohydroxysinapinic acid groups or that these substances are enclosed in particle-, vesicle-, or liposome-like adhesion promoters.

16. The coating according to claim 1, wherein said polymeric adhesion promoter layer contain pharmaceutically active -substances in covalently and/or noncovalently bound form.

17. The coating according to claim 16, wherein said polymeric adhesion promoter layer consists of alternating polymer- and/or particle-layers.

18. The coating according to claim 1, wherein said substrate consists of a conducting material, a glass or another oxidic material, which can additionally be silanized, a noble metal, that can additionally be functionalized with an alcylmercaptane, a plastic material, of natural fibers and/or artificial fibers.

19. The coating according to claim 18, wherein said substrate is cleaned and/or functionalized by oxidizing substances, with plasma and/or ionizing radiation.

20. The coating according to claim 1, wherein said substrate consists of nano- and/or microparticles.

* * * * *